United States Patent [19]
McDow et al.

[11] Patent Number: 5,487,871
[45] Date of Patent: Jan. 30, 1996

[54] MERCURY ASSAY

[75] Inventors: Timothy S. McDow, Palm Beach Gardens; Marlin Bensinger, Lake Worth, both of Fla.

[73] Assignee: LDC Analytical, Inc., Lake Worth, Fla.

[21] Appl. No.: 969,000

[22] Filed: Oct. 30, 1992

[51] Int. Cl.⁶ ............................................. G01N 21/31
[52] U.S. Cl. .................... 422/80; 422/81; 422/82.09; 422/231
[58] Field of Search ............................ 422/68.1, 82.05, 422/82.09, 231, 80; 456/81

[56] References Cited

U.S. PATENT DOCUMENTS

| | | | |
|---|---|---|---|
| 3,826,614 | 5/1972 | Capuano | 436/81 |
| 3,884,639 | 5/1975 | Sugiyama | 23/230 PC |
| 4,023,929 | 5/1977 | Becker et al. | 23/230 PC |
| 4,534,940 | 8/1985 | Bourcier | 422/68 |
| 4,959,334 | 9/1990 | Mauleon et al. | 422/144 |

OTHER PUBLICATIONS

Mercury Analysis in Water by manual Cold Vapor Techinque, Method 245.1 CLP–M (Manual Cold Vapor Technique), D–46—D–57.

*Primary Examiner*—David A. Redding
*Attorney, Agent, or Firm*—Fish & Richardson

[57] ABSTRACT

An automated cold vapor mercury assay system includes a sample inlet, a storage chamber of predetermined volume for storing a sample of material to be analyzed, a reaction chamber having first and second inlet ports and an outlet port, a reducing agent reservoir, a transport liquid reservoir, a distributor coupled to the sample storage chamber and movable between a first position connecting the storage chamber to the sample inlet and a second position connecting the storage chamber to the reaction chamber, analyzer apparatus coupled to the outlet port of the reaction chamber structure, and controller structure.

18 Claims, 3 Drawing Sheets

5,487,871

MERCURY ASSAY

BACKGROUND AND SUMMARY OF THE INVENTION

This invention relates to analytical systems and processes, and more particularly to systems and processes for the analysis of materials for mercury content.

Mercury is generally found as ionic or organic mercury in nature. Examples of ionic mercury include inorganic compounds in rocks and mercury salts in water. When a strong acid is added to such materials, the products can be made water soluble with the resulting mercury cations being completely dissociated from the counter group anions. Analysis of mercury in the cation state may be performed by the cold vapor (room temperature) method which involves adding a strong reducing agent such as stannous chloride to the sample mixture to convert mercury cations to elemental mercury which is insoluble in aqueous solution. The resulting elemental mercury vaporizes in air in a manner similar to water evaporating, and the vaporized mercury may be analyzed in an atomic absorption system by passing the vaporized mercury through a beam of light with a spectral wavelength of 253.7 nanometers.

In environmental pollution investigations, mercury is most often found as part of an organic compound in forms such as phenyl mercury or methyl mercury. Organo-substituted mercury compounds must be treated by a more vigorous procedure than described above that includes the steps of digestion by a strong acid or base and then breaking apart with a strong oxidizer such as permanganate, bromate or vanadium pentoxide, with the subsequent elimination of excess oxidant by the addition of hydroxyl ammonium chloride. Among aspects that complicate mercury assays are the facts that nearly everything contains some trace level of mercury, and that compounds other than mercury can absorb radiation at 253.7 nanometers and give a "false positive" for mercury.

An EPA Protocol describes a manual mercury analysis by cold vapor technique that involves placing a sample aliquot diluted to 100 mL in a 300 mL bottle; adding reagents including 5 mL of stannous sulfate; immediately attaching the bottle to aeration apparatus; aerating the bottle with a circulating pump; and passing the resulting vapor through a desiccant chamber and an absorption cell to a scrubber.

In accordance with one aspect of the invention, there is provided an automated cold vapor mercury assay system that includes a sample inlet, a storage chamber of predetermined volume for storing a sample of material to be analyzed, a reaction chamber having first and second inlet ports and an outlet port, a reducing agent reservoir, a transport liquid reservoir, distributor structure coupled to the sample storage chamber and movable between a first position connecting the storage chamber to the sample inlet and a second position connecting the storage chamber to the reaction chamber, analyzer apparatus coupled to the outlet port of the reaction chamber structure, and controller structure. The controller in an analysis sequence places the distributor in the first position for flowing sample to be analyzed into the storage chamber structure from the sample inlet while concurrently flowing a reducing agent from the reducing agent reservoir structure into the reaction chamber structure; then supplies a source of gas for flow through the reaction chamber to release residual elemental mercury from the reducing. agent; then moves the distributor to the second position and applies transport liquid through the distributor to the storage chamber for flowing the sample to be analyzed into the reaction chamber through the second inlet port; and again applies agitating gas to agitate the material in the reaction chamber to form elemental mercury vapor for transport to the analyzer apparatus for analysis.

In accordance with another aspect of the invention, there is provided an automated cold vapor mercury assay system that includes a sample inlet, a storage chamber of predetermined volume for storing a sample of material to be analyzed, a reaction chamber having first and second inlet ports and an outlet port, a reducing agent reservoir, a transport liquid reservoir, distributor structure coupled to the sample storage chamber and movable between a first position connecting the storage chamber to the sample inlet and a second position connecting the storage chamber to the reaction chamber, analyzer apparatus coupled to the outlet port of the reaction chamber, and conduit structure coupled between the analyzer apparatus and the first reaction chamber inlet port of said for obtaining a reference value of agitating gas and then applying the agitating gas to material in the reaction chamber structure.

In accordance with another aspect of the invention, there is provided a cold vapor mercury assay system that includes a sample inlet, a storage chamber of predetermined volume for storing a sample of material to be analyzed, a reaction chamber having first and second inlet ports and an outlet port, and analyzer apparatus coupled to the outlet port of the reaction chamber. The reaction chamber includes a body portion of cylindrical configuration in which a sample inlet is coupled for tangential introduction of sample material to be assayed; a base portion of hemispherical configuration in which a reagent inlet port is formed, and an upper portion of conical configuration to which an outlet port is coupled, the conical upper portion having an inner surface of concave configuration.

In preferred embodiments, the storage chamber has a volume of less than ten milliliters, and the reaction chamber has a volume of less than fifty milliliters but greater than that of the storage chamber. Dryer material is coupled in circuit between the reaction chamber outlet port and the analyzer apparatus. The agitating gas is preferably selected from the group consisting of nitrogen, helium, argon, and air and has a purity of at least 0.998.

In a particular embodiment, the analyzer is of the atomic absorption type and includes a light source for generating a beam of light with a spectral wavelength of 253.7 nanometers; first and second photosensors; and an analysis cell with two parallel passages disposed between the radiation source and the radiation sensors, and each passage has an aspect ratio (length/diameter) of at least one hundred. The body portion of the reaction chamber has a diameter of less than five centimeters and a length in the range of three to eight centimeters; the base portion is hemispherical and has a radius of less than three centimeters and a first inlet port is disposed at the bottom of the base portion; and the upper portion has a length in the range of three to six centimeters and a concave inner surface that tapers smoothly from said body portion to said outlet port at the top of said upper portion. Autosampler structure is coupled to a first port of the distributor and reduced pressure applying apparatus is coupled to a second port of the distributor for drawing a sample from the autosampler into the storage chamber when the distributor is in its first position.

The small internal volumes in the particular embodiment enable the system to measure very low levels of mercury (one part per trillion). Minimal volumes are provided throughout the system. The largest volume in the system is the reaction chamber, and the concave shape of upper portion of that chamber contributes to the small internal volume. That system has a detection limit of less than one part per trillion.

BRIEF DESCRIPTION OF THE DRAWINGS

Other features and advantages of the invention will be seen as the following description of a particular embodiment progress, in conjunction with the drawings, in which.

DESCRIPTION OF PARTICULAR EMBODIMENT

Figure 1:
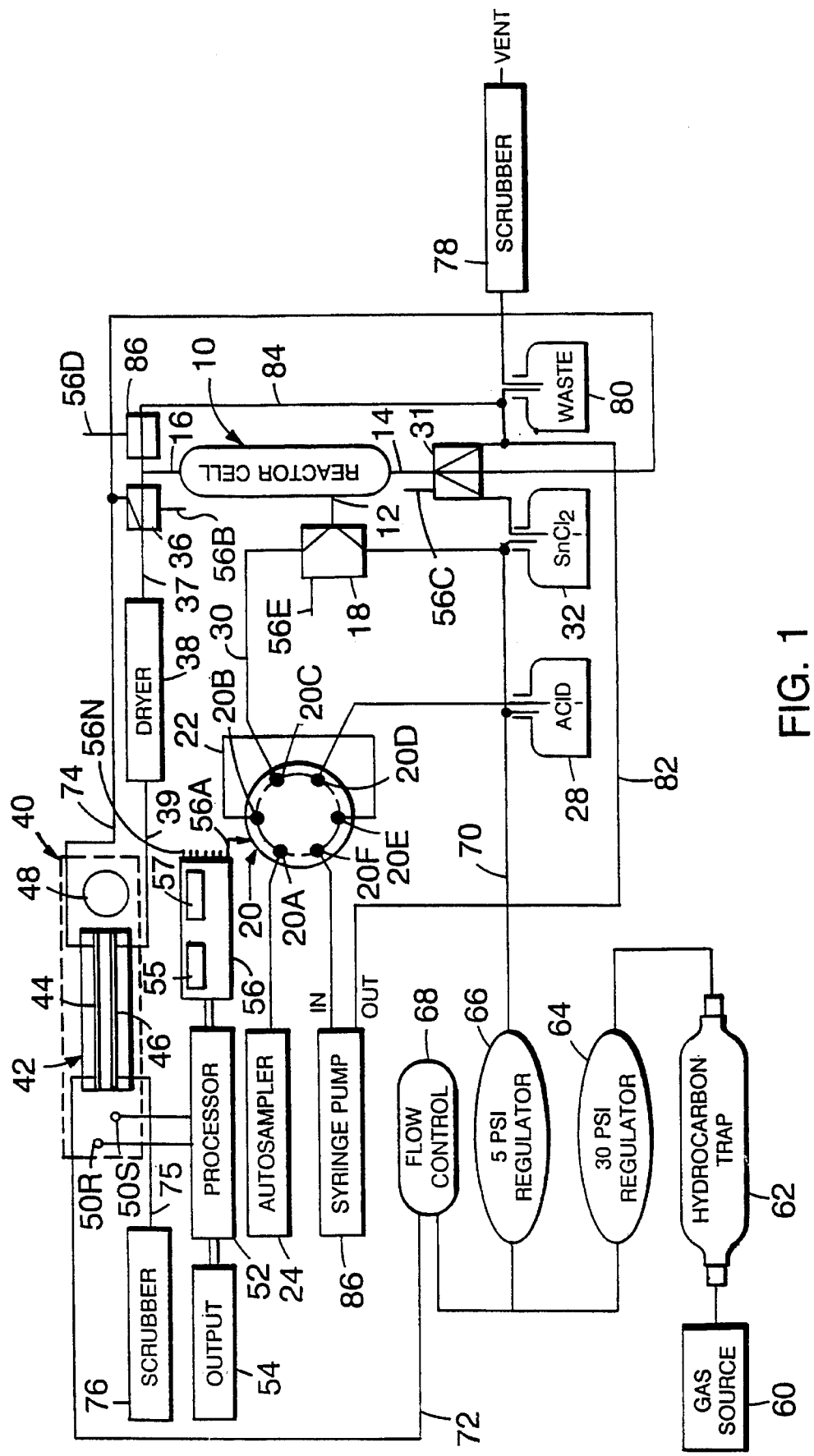
FIG. 1 is a schematic diagram of a cold vapor mercury assay system in accordance with the invention.

The cold vapor mercury assay system shown in FIG. 1 includes reaction chamber 10 with sample inlet 12, reactant and gas inlet 14, and outlet 16. Connected to sample inlet 12 through valve 18 is distributor 20 to which is coupled sample loop 22 (of one-half, one, or five milliliter volume depending on the level of mercury concentration in the sample to be analyzed. When the sample loop volume changed, the new volume is communicated to controller 56 and outputs of the controller then compensate for the different sample volume.) Distributor 20 includes port 20A coupled to autosampler 24; ports 20B and 20E to which sample loop 22 is coupled; port 20F to which syringe (reduced pressure) pump 26 is coupled; port 20D to which an acid transport liquid line from reservoir 28 is coupled; and port 20C that is connected by line 30 through valve 18 to sample inlet 12 of reaction chamber 10. Reaction chamber inlet 14 is coupled through three-way valve 31 to reducing agent (stannous chloride) reservoir 32, to feedback line 74 and to waste 80. The acid in reservoir 28 is ten percent sulfuric acid solution; and the stannous chloride reducing solution in reservoir 32 is a solution of five percent $SnCl_2$ and sulfuric acid.

Reaction chamber outlet 16 is coupled through two way valve 36, magnesium perchlorate dryer chamber 38 (for trapping acid constituents of the vapor flowing from reaction chamber 10), and sample line 39 for applying elemental mercury vapor from chamber 10 to atomic absorption analyzer 40. Analyzer 40 includes high aspect ratio analysis cell 42 which has two parallel bores 44, 46 (each of two millimeter diameter and ten centimeters length) light source 48 (a low pressure mercury lamp that provides the 253.7 nanometer atomic line of mercury); and photodiode sensors 50R and 50S that respond to light beam passed through bores 44, 46 and provide outputs to processor 52 for application to output device 54. Controller 56 provides control outputs on lines 56A–56N, and has control inputs 55A–F and indicators 57A–L (FIG. 2).

A clean gas (e.g., nitrogen, helium, argon or air) is flowed at a rate of about 200 milliliters per minute from source 60 through hydrocarbon trap 62 (which contains activated charcoal for eliminating organic contaminants from the gas stream) and thirty psi regulator 64 to five psi regulator 66 and flow control 68. Five psi gas is supplied over line 70 to acid reservoir 28, stannous chloride reservoir 32, and valve 18; and the gas flow from flow control 68 is applied over line 72 for flow through analysis cell reference bore 44 to outlet line 74 for application to valve 31 for flow through chamber 10 and to valve 36 for flow through dryer tube 38 and line 39 to sample bore 46 and then discharge over line 75 to scrubber 76.

Waste chamber 80 is connected through scrubber 78 to a vent and has an inlet coupled over line 82 from syringe pump 26; and second inlet over line 84 that is coupled through valve 86 to outlet 16 of reaction chamber 10.

Figure 2:
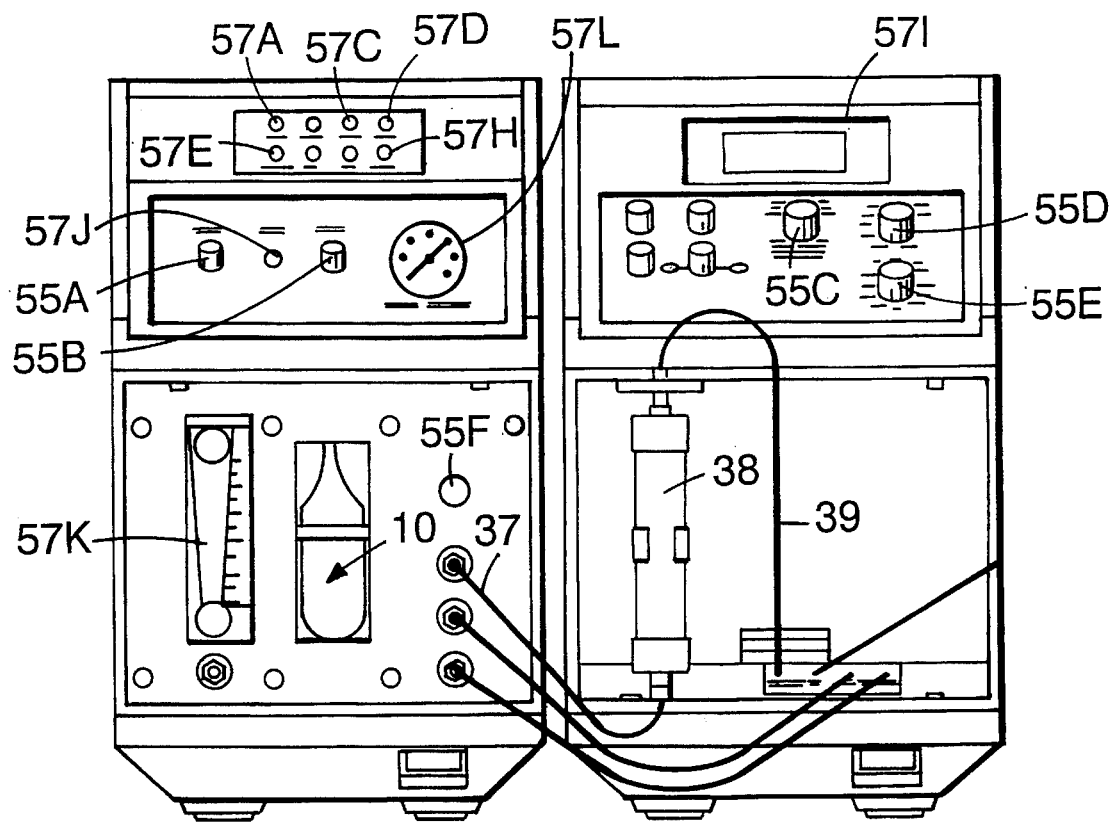
FIG. 2 is a front elevational view of components of the system shown in FIG. 1.

Components of the system are shown in front view in FIG. 2.

Further aspects of reaction chamber 10 may be seen with reference to FIGS. 3–7. Chamber 10 is constructed of 1.5 millimeter thick Pyrex glass and has a cylindrical body portion 90 that has a diameter of about 2.5 centimeters and a length of about five centimeters; a base portion 92 of hemispherical configuration with a radius of about 1.25 centimeters; and upper portion 94 that includes a conical transition section 96 with a smooth concave inner surface 97, and is about four centimeters long and transitions from the body portion diameter of about 2.5 centimeters to outlet tube 98 of about 0.2 centimeter diameter. Ten millimeter frit filter 100 (of 0.01 porosity) is disposed at the base of portion 92 and connected to arm 102 in which inlet port 14 is formed. Sample inlet tube 104 extends from sample inlet port 12 to body portion 90 and is disposed in tangential relationship to the inner surface of cylindrical body 90 (FIG. 5); and outlet arm 98 extends from the upper end of chamber 10 to outlet port 16. Each tube arm 98, 102 and 104 has an inner diameter of about two millimeters.

Figure 6:
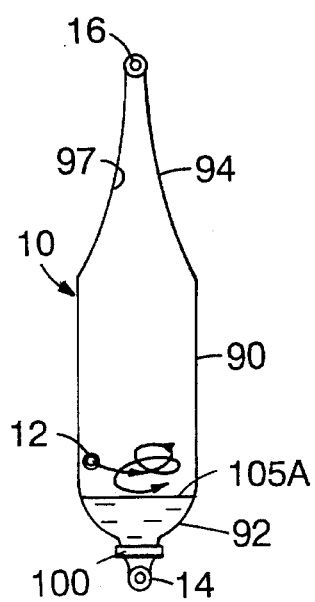
FIGS. 6–8 are diagrammatic views of flow paths of material within the reaction chamber.
Figure 7:
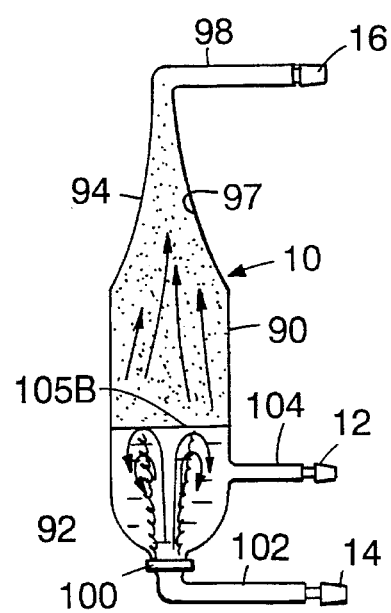

In system operation, the sample to be analyzed is predigested with an appropriate acid or other reagent in a heated bath at 90° C. for two hours and applied to autosampler 24. (Autosampler 24 is used to present a series of predigested samples (e.g., 114 8ml tubes in normal mode or 27 28ml tubes in high sensitivity mode (with a five millimeter sample loop)). Sample loop 22 is filled with the sample from autosampler 24 or other inlet structure through distributor 20 (as set in intake mode by a signal over line 56A from controller 56) in response to reduced pressure applied by syringe pump 26 to suck sample from a sample tube in autosampler 24 through inlet 20A to port 20B, to load sample loop 22 and then through port 20E and out port 20F to pump 26 for discharge over line 82 to waste 80. Concurrently, reservoirs 28 and 32 are pressurized with 5 psi gas from regulator 66 over line 70 and the pure reference gas is flowed through flow control 68 and line 72 through analysis cell reference bore 44 and return through valve 36 controlled in response to a signal over control line 56B and sample bore 46 for discharge to scrubber 76 to provide background reference signals at sensors 50R&S. Concurrently, 2.5 milliliters of stannous chloride reducing mixture from reservoir 32 is flowed through valve 31 controlled in response to a signal over control line 56C and filter 100 into base portion 92 of reaction chamber 10 to a fill level 105A below the tangential sample inlet line 104 (as indicated in FIG. 6) and then valves 31 and 36 are switched by controller 56 to admit gas (for about one minute) over lines 74 and 14 into chamber 10 for bubbling flow through the stannous chloride liquid for converting any residual mercury in the stannous chloride to elemental mercury vapor and out of chamber 10 to line 16 and through valve 36, dryer 38, and bore 46 for measurement by detector 50S (peak 106 in the response curve of FIG. 9).

Figure 5:
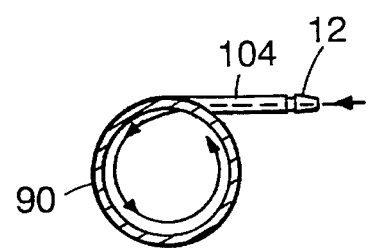
FIG. 5 is a sectional view taken along the line 5—5 of FIG. 4.

Controller 56 then switches valve 36, opens vent valve 86 controlled in response to a signal over control line 56D, and shifts distributor 20 controlled in response to a signal over control line 56A to connect transport liquid port 20D in series with sample loop 22 through ports 20E and 20B for discharge through outlet port 20C, line 30 and valve 18 to sample inlet 12. The pressurized acid transport liquid from reservoir 28 flows the sample in loop 22 out through line 30 into reaction chamber 10 in tangential swirling action as indicated in FIGS. 5 and 6 with a volume of acid that is five times the volume of the sample loop 22. Open vent valve 86 allows venting of the reaction chamber 10 to waste 80 as the sample mixture is flowed into the reaction chamber 10 and reaction chamber 10 is filled to a level 105B, 105C in the body portion 90 depending on the volume of the sample loop 22 employed (½ milliliter, one milliliter (level 105B-FIG. 7) or five milliliters (level 105C-FIG. 8)).

To minimize contamination between samples, the acid transport liquid from reservoir 28 is used as a cleaning agent as well as to ensure adequate sample transfer. Further, a wash station may be used on autosampler 24.

After the sample has been introduced into chamber 10 for reaction with the $SnCl_2$ reducing agent, valve 36 is switched by a signal on control line 56B from feedback mode to the sample chamber outlet port 16 and a precision regulated gas flow is again supplied to the bottom port 14 through valve 31 by a signal on control line 56C. The gas flow through 10mm frit (porous stone) filter 100 causes an optimized dispersion of gas bubbles that vigorously agitates the fluid. This agitation causes vortex mixing action (FIGS. 7 and 8) that circulates the fluid, ensuring that a complete chemical reaction takes place (with associated release of elemental mercury) in the reaction chamber. The hemispherical base 92 of chamber 10 avoids dead space where fluid could otherwise get trapped during the vortex mixing. During the reaction, the precision gas supply is used as a carrier to sweep the elemental mercury (in its vapor state) from chamber 10 through magnesium perchlorate dryer tube 38 into detector 40 for quantitative analysis. The aerodynamic shape of the top portion 94 of chamber 10 ensures a smooth flow path for mercury vapor, acts as a condenser to remove acid liquid from the gas stream, and minimizes the internal dead volume to ensure good mercury peak definition with very low concentrations.

As the gas bubbles burst on the top of the liquid (level 105B or 105C in chamber 10), droplets of reactant liquid rise with the gas stream, and if not impeded will be swept out to the dryer tube 38. The concave surface 97 causes these droplets to hit the sides of the glass and to drain back towards the base portion 92 of the chamber 10 (FIG. 8), substantially decreasing the moisture content in the gas stream and significantly increasing the life of the magnesium perchlorate in dryer tube 38.

Figure 8:
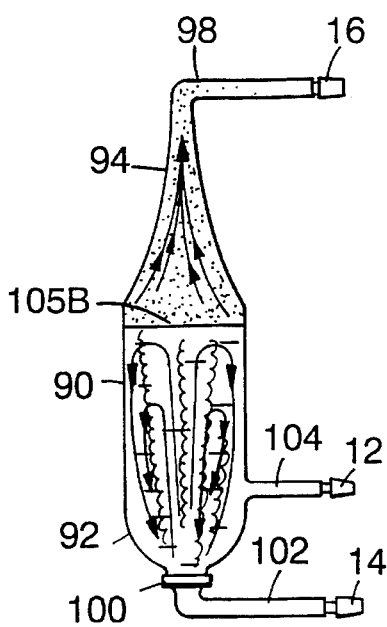

The small internal volumes enable the system to measure very low levels of mercury (one part per trillion). Minimal volumes exist throughout the system. The largest volume in the system is the reaction chamber 10, and the concave shape of upper portion 94 contributes to the small internal volume. The system has a detection limit of less than one part per trillion. When the system is used to look for low amounts of mercury, larger sample loop volumes are used (5 ml of sample), thus raising the fluid to level 105C as shown in FIG. 8.

Figure 9:
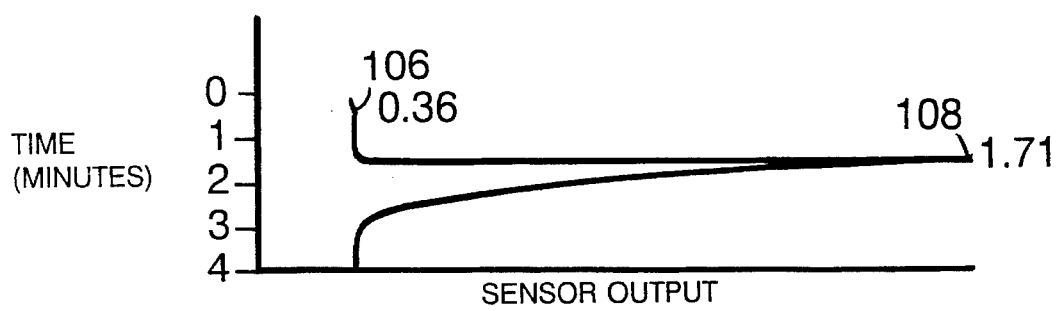
FIG. 9 is a diagram of the response of the system shown in FIGS. 1 and 2 to a 0.1 ppm mecuric chloride standard in ten percent $H_2SO_4$.
Figure 3:
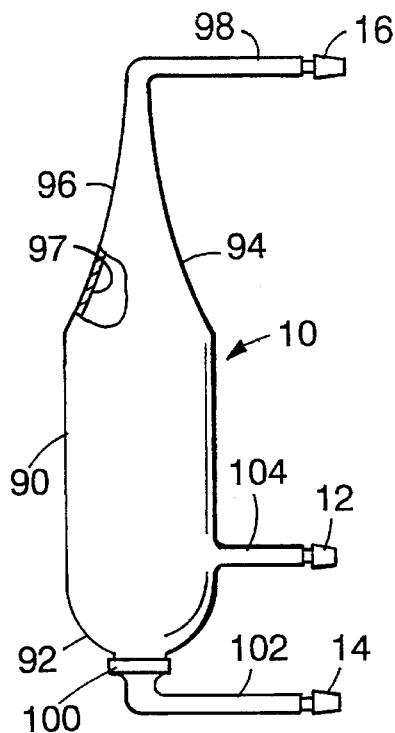
FIG. 3 is a front elevational view of the reaction chamber employed in the system of FIG. 1.
Figure 4:
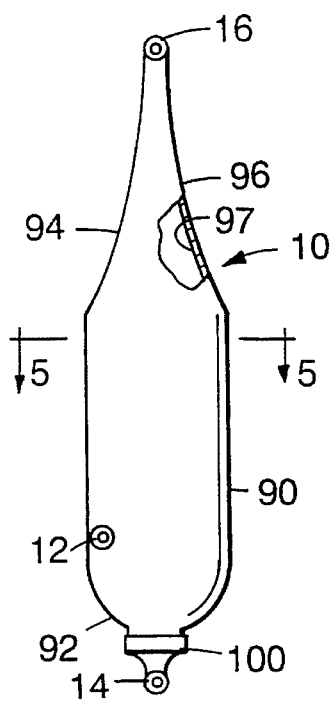
FIG. 4 is a side elevational view of the reaction chamber of FIG. 3.

A typical detector response is shown in FIG. 9 with peak 106 being generated about twenty seconds after the gas from source 60 is initially bubbled through the stannous chloride solution and the peak 108 being generated about one minute later (about ten seconds after the sample was introduced into the chamber 10). The sample was a 0.1 ppm mecuric chloride standard in ten percent $H_2SO_4$ and the aeration gas was ultra high purity nitrogen.

At the end of the elemental mercury vapor transfer cycle, controller 56 causes the contents of the reaction chamber 10 to be evacuated to waste reservoir 80 with low pressure gas supplied through line 70 and valve 18; the ready LED 57J is energized at the end of the waste cycle and start button 55A may be depressed to start the next cycle.

While a particular embodiment of the invention has been shown and described, various modifications of that embodiment will be apparent to those skilled in the art, and therefore, it is not intended that the invention be limited to the disclosed embodiment, or to details thereof, and departures may be made therefrom within the spirit and scope of the invention.

What is claimed is:

1. An automated cold vapor mercury assay system comprising
   sample inlet structure,
   storage chamber structure of predetermined volume for storing a sample of material to be analyzed,
   reaction chamber structure having first and second inlet ports and an outlet port and defining a reaction chamber,
   reducing agent reservoir structure,
   transport liquid reservoir structure,
   a distributor coupled to said sample storage chamber structure and movable between a first position connecting said storage chamber structure to said sample inlet structure and a second position connecting said storage chamber structure to said reaction chamber structure,
   mercury vapor analyzer apparatus coupled to said outlet port of said reaction chamber structure, and
   controller structure for placing said distributor in said first position for flowing sample to be analyzed into said storage chamber structure from said sample inlet structure while concurrently flowing a reducing agent from said reducing agent reservoir structure into said reaction chamber, for supplying a source of gas for flow through said reaction chamber to release residual elemental mercury from the reducing agents, for moving said distributor to said second position and applying transport liquid through said distributor to said storage chamber structure for flowing said sample to be analyzed into said reaction chamber through said second inlet ports, and for then applying an agitating gas to said first port to agitate the material in said reaction chamber to form elemental mercury vapor for transportation to said analyzer apparatus.

2. The system of claim 1 wherein said storage chamber structure has a volume of less than ten milliliters.

3. The system of claim 1 wherein said reaction chamber structure includes a body portion of cylindrical configuration in which said second port is disposed for introduction of sample material to be assayed in a direction tangential to the cylindrical inner surface of said body portion;
   a base portion of hemispherical configuration in which said first inlet port is provided; and an upper portion of concave conical configuration to which said outlet port is coupled.

4. The system of claim 3 wherein said reaction chamber has a volume of less than fifty milliliters.

5. The system of claim 1 wherein said analyzer is of the atomic absorption type and includes a light source for generating a beam of light with a spectral wavelength of 253.7 nanometers; first and second photosensors; and an analysis cell with two parallel passages disposed between said radiation source and said radiation sensors, each said passage having an aspect ratio (length\diameter) of at least one hundred.

6. The system of claim 1 and further including dryer material coupled in circuit between said outlet port of said reaction chamber structure and said analyzer apparatus.

7. The system of claim 1 wherein said agitating gas is selected from the group consisting of nitrogen, helium, argon, and air.

8. The system of claim 1 wherein said agitating gas has a purity of at least 0.998.

9. The system as claimed in claim 3 wherein said body portion of said reaction chamber structure has a diameter of less than five centimeters and a length in the range of three to eight centimeters;

said base portion has a radius of less than three centimeters and said first port is disposed at the bottom of said hemispherical base portion; and said concave conical upper portion has a length in the range of three to six centimeters and a concave inner surface that tapers smoothly from said body portion to said outlet port at the top of said upper portion.

10. The system of claim 1 and wherein said sample inlet structure includes autosampler structure coupled to a first port of said distributor and reduced pressure applying apparatus coupled to a second port of said distributor for drawing a sample from said autosampler structure into said sample chamber structure when said distributor is in said first position.

11. The system of claim 1 and further including conduit structure coupled between said analyzer apparatus and said first inlet port of said reaction chamber for obtaining a reference value of the agitating gas and then applying said agitating gas to material in said reaction chamber structure.

12. An automated cold vapor mercury assay system comprising sample inlet structure, storage chamber structure of predetermined volume for storing a sample of material to be analyzed, reaction chamber structure having first and second inlet ports and an outlet port and defining a reaction chamber;

reducing agent reservoir structure, transport liquid reservoir structure, a distributor coupled to said sample storage chamber structure and movable between a first position connecting said storage chamber structure to said sample inlet structure and a second position connecting said storage chamber structure to said reaction chamber structure, mercury vapor analyzer apparatus coupled to said outlet port of said reaction chamber structure, and conduit structure coupled between said analyzer apparatus and said first inlet port of said reaction chamber for obtaining a reference value of the agitating gas and then applying said agitating gas to material in said reaction chamber.

13. The system of claim 12 wherein said analyzer apparatus is of the atomic absorption type and includes a light source for generating a beam of light with a spectral wavelength of 253.7 nanometers; first and second photosensors; and an analysis cell with two parallel passages disposed between said radiation source and said radiation sensors, each said passage having an aspect ratio (length\diameter) of at least one hundred.

14. The system of claim 13 and further including dryer material coupled in circuit between said outlet port of said reaction chamber structure and said analyzer apparatus.

15. The system of claim 12 wherein said storage chamber structure has a volume of less than ten milliliters, and said reaction chamber has a volume of less than fifty milliliters.

16. The system of claim 15 wherein said agitating gas is selected from the group consisting of nitrogen, helium, argon, and air, and said gas has a purity of at least 0.998.

17. A cold vapor mercury assay system comprising storage chamber structure of predetermined volume for storing a sample of material to be analyzed, reaction chamber structure having first and second inlet ports and an outlet port, said reaction chamber structure including a body portion of cylindrical configuration to which said first inlet port is coupled for introduction of sample material to be an assayed in a direction tangential to the cylindrical inner surface of said body portion, a base portion of hemispherical configuration to which said second inlet port is coupled, and an upper portion of concave conical configuration to which an outlet port is coupled, and mercury vapor analyzer apparatus coupled to said outlet port of said reaction chamber structure.

18. The system as claimed in claim 17 wherein said body portion of said reaction chamber structure has a diameter of less than five centimeters and a length in the range of three to eight centimeters; said base portion has a radius of less than three centimeters and said first port is disposed at the bottom of said hemispherical base portion; and said concave conical upper portion has a length in the range of three to six centimeters and a concave inner surface that tapers smoothly from said body portion to said outlet port at the top of said upper portion.

* * * * *